United States Patent
Abraham-Fuchs et al.

(10) Patent No.: US 6,206,840 B1
(45) Date of Patent: Mar. 27, 2001

(54) METHOD FOR THE IDENTIFICATION OF A LIQUID SECRETED BY A LIVING SUBJECT PARTICULARLY FOR IDENTIFICATION OF AMNIOTIC FLUID

(75) Inventors: Klaus Abraham-Fuchs; Kai-Uwe Schmidt; Joachim Tork, all of Erlangen; Helge Binder; Ludwig Wildt, both of Herzogenaurach, all of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/373,110

(22) Filed: Aug. 12, 1999

(30) Foreign Application Priority Data

Aug. 12, 1998 (DE) .............................. 198 36 591
May 7, 1999 (EP) ................................ 99109096

(51) Int. Cl.⁷ ...................................... A61B 5/00
(52) U.S. Cl. ..................... 600/584; 600/309; 128/898
(58) Field of Search .................... 600/304, 309, 600/584; 128/898; 422/50, 68.1; 436/63, 65

(56) References Cited

U.S. PATENT DOCUMENTS

| | | | |
|---|---|---|---|
| 4,895,017 | 1/1990 | Pyke et al. | 73/23 |
| 5,284,749 | * 2/1994 | Cowley et al. | 435/7.1 |
| 5,726,026 | * 3/1998 | Wilding et al. | 435/7.21 |
| 5,837,546 | * 11/1998 | Allen et al. | 436/169 |
| 6,016,712 | * 1/2000 | Warden et al. | 73/864.21 |
| 6,027,942 | * 2/2000 | Hutchens et al. | 436/173 |

FOREIGN PATENT DOCUMENTS

| | | |
|---|---|---|
| 37 06 372 | 1/1989 | (DE) . |
| 44 07 217 | 9/1995 | (DE) . |
| 0 527 258 | 2/1993 | (EP) . |
| WO 99/42820 | 8/1999 | (WO) . |

OTHER PUBLICATIONS

"Technik der Geruchserkennung," Asche, CLB Chemie in Labor und Biotechnik, vol. 48, No. 7 (1997), pp. 302–304.
A Perfume Odour–sensing System Using an Array of Piezo-electric Crystal Sensors with Plasticized PVC Coatings, Cao et al., Fresenius J. Anal. Chem., vol. 355 (1996) pp. 194–199.
"Electronic Noses—Development and Future Prospects," Craven et al., Trends in Analytical Chemistry, vol. 15 (1996) pp. 486–493.
"Wie menschlich sind electronische Nasen?", Schweizer–Berberich et al., tm–Technisches Messen, vol. 62 (1995), pp. 237–249.
"Evaluation of Gas–liquid Chromatography for the Rapid Diagnosis of Amniotic Fluid Infection: a Preliminary Report," Wager et al., American Journal of Obstetrics and Gynecology, Vo. 152 (1985), pp. 51–56.
"The Clinical Value of Gas–Liquid Chromatography in the Detection of Intra–Amniotic Microbial Invasion," Romero et al., Obstetrics and Gynecology, vol. 72 (1988), pp. 44–50.
Manual for MOSES II Gas Analysis System.
"Electronic Noses and Their Applications," Keller et al., Conference Record of Northcon (IEEE, Oct. 10, 1995), pp. 116–119.
"Hybrid Modular Sensor Systems: A New Generation of Electronic Noses," Mitrovics et al., IEEE International Symposium on Industrial Electronics (ISIE '97), 1997 Conference Proceedings, pp. 116–121.

(List continued on next page.)

Primary Examiner—Cary O'Connor
Assistant Examiner—Charles Marmor, II
(74) Attorney, Agent, or Firm—Schiff Hardin & Waite

(57) ABSTRACT

In a method for identifying a liquid secreted by a living subject, particularly amniotic fluid, the liquid is identified by means of its characteristic volatile constituents.

11 Claims, 1 Drawing Sheet

OTHER PUBLICATIONS

"Odours and Flavours Identified with Hybrid Modular Sensor Systems," Ulmer et al., Sensors and Actuators, vol. 43, No. 1–3 (1997), pp. 24–33.

"Current Trends in 'Artificial–Nose' Technology," Dickinson et al., Trends in Biotechnology, vol. 16, No. 6 (Jun., 1998), pp. 250–258.

* cited by examiner

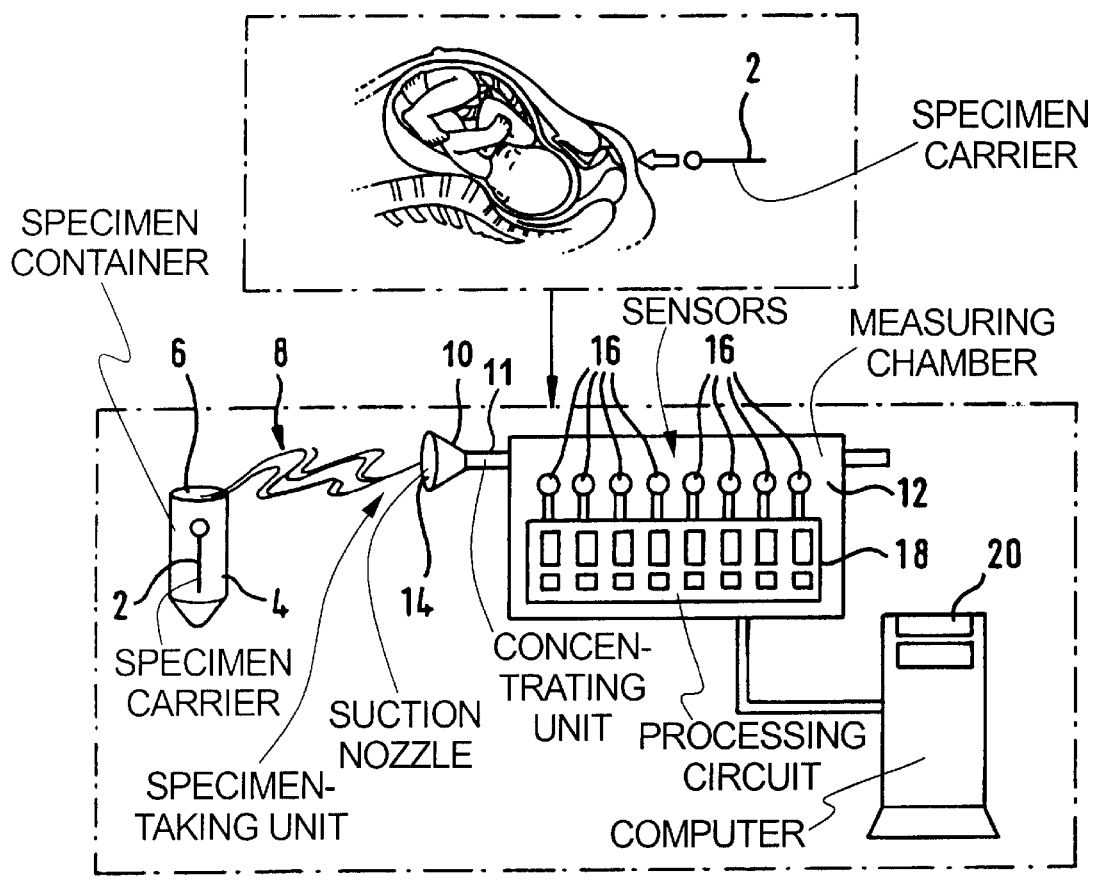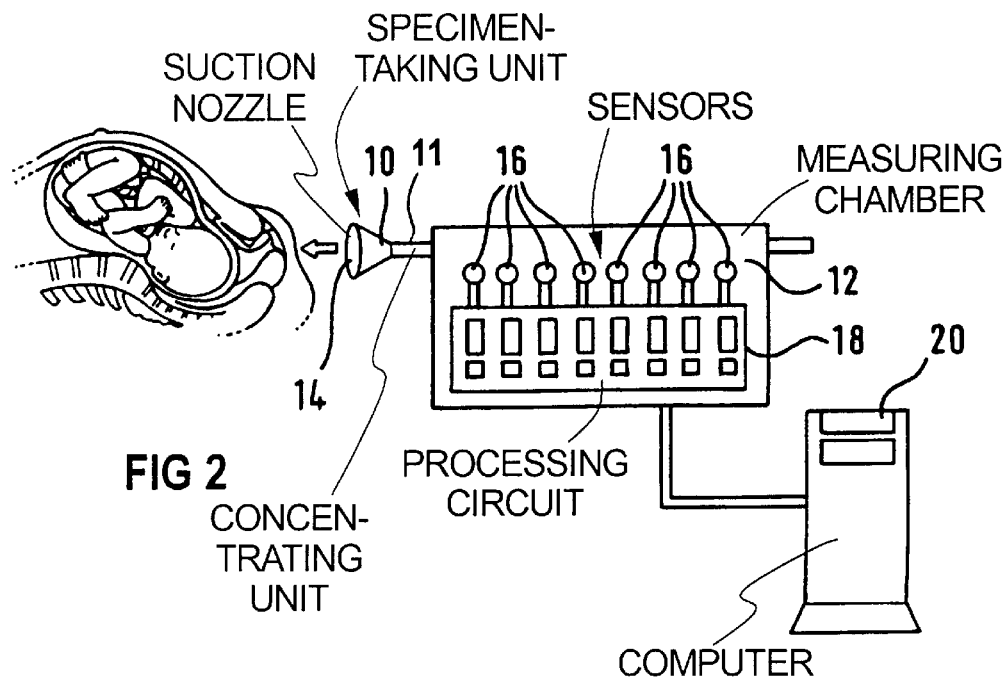

US 6,206,840 B1

METHOD FOR THE IDENTIFICATION OF A LIQUID SECRETED BY A LIVING SUBJECT PARTICULARLY FOR IDENTIFICATION OF AMNIOTIC FLUID

BACKGROUND OF THE INVENTION

1. Field of the Invention

The present invention is directed to a method for the identification of a liquid secreted by a living subject, particularly amniotic fluid, and is also directed to an apparatus for implementation of the method.

2. Description of the Prior Art

During a pregnancy, a premature rupture of the amnion can occur, which is the loss of amniotic fluid with opening the water bag without the uterus being in labor. The clinical reason for a premature rupture of the amnion is that a path through the vagina between the exterior environment and the intra-uterine embryonic region is established, and as a result the access of bacteria with subsequent intra-uterine infection becomes possible. An intra-uterine infection can be life-threatening for the child as well as for the mother, and moreover can lead to permanent sterility.

Whereas manifest rupture of the amnion with some loss of amniotic fluid raises no diagnostic problems, a so-called high rupture of the amnion often can be detected only with great difficulty. Patients report a loss of fluid, but it is not clear whether it is amniotic fluid, urine or vaginal secretion.

The detection of premature rupture of the amnion is of substantial clinical significance in natal care. The risks that are associated with an unrecognized rupture of the amnion are serious and life-threatening under certain circumstances. Particularly in the early stages of pregnancy, they can result in a premature birth with all of the accompanying phenomena. The reliable exclusion of a premature rupture of the amnion is likewise of great significance since corresponding symptoms (loss of fluid) are frequently observed and unnecessary, non-temporary admission into a hospital with the corresponding discomfort and cost often arises.

Various methods have been utilized for detecting amniotic fluid. These are essentially based on the detection of substances that are contained in high concentration in amniotic fluid but do not occur in vaginal secretion. Included, for example, are prolacitin, human choriongonadotropine (HCG), alpha-feto-protein (AFP) and other pregnancy-specific proteins. The problems in detecting these substances are due to the fact that these substances very quickly decompose in acidic vaginal secretion and then no longer can be detected; and the detection of these proteins is often not simple to implement in terms of methodology.

A further possibility for diagnosis is to conduct ultrasound examinations. An attempt is thereby made to provoke a discharge of amniotic fluid toward the outside along the water bag by pressing and shaking the lower torso. If such a discharge occurs it should be perceptible in the ultrasound image.

Another possibility for diagnosis is to make use of the fact that the amniotic fluid has an alkaline pH value. This is checked with a litmus test of the vaginal fluid.

German PS 37 06 372 discloses a method and an apparatus for signaling birth in animals, particularly in dogs. The method identifies the suddenly-increasing atmospheric humidity which occurs due to the amniotic fluid being released at birth, and an acoustic and/or optical signal is triggered immediately thereafter. An apparatus for the implementation of the method has a humidistat arranged within the animals's habitat, such as a doghouse or the like, preferably in the ceiling region, this being connected to an electrically actuatable evaluation device that registers sudden changes in atmospheric humidity. This evaluation device is connected in pulse-generating fashion to a signal sensor provided outside the habitat. This method and this device, however, are not suitable for identifying a liquid secreted by a living subject. Since living subjects are composed of 70–80% water, they are always moist. The presence of moisture is not characteristic of a specific, secreted fluid; rather, no distinction can be made as to whether the fluid, even if detected, is amniotic fluid, urine or vaginal secretion.

The term "electronic nose" describes sensor systems that are close to the human olfactory sense in terms of their functioning. By contrast to gas chromatography or mass spectrometry, they do not detect individual components of a gas but detect aggregate parameters. A so-called fingerprint of the scent is registered. The results are differently presented dependent on the type of evaluation.

The article by M. A. Craven, J. W. Gardner, P. N. Bartlett, "Electronic Noses—Development and Future Prospects", which appeared in Trends in Analytical Chemistry, Vol. 355 (1996), pp. 486–493, indicates that commercial devices that are called electronic noses are now being utilized in a number of industrial fields such as food processing, water handling, and brewing. Medical diagnostics is also cited therein as a possible, future field of employment of electronic noses.

SUMMARY OF THE INVENTION

An object of the present invention is to provide a method and an apparatus with which a liquid secreted by a life form, particularly amniotic fluid, can be identified in a simple way.

This object is achieved in a method in accordance with the invention wherein the fluid is identified by its characteristic, volatile constituents. This is based on the experience that such fluids have a characteristic odor independently of the individual. Differentiated according to their contents, the fluids have a specific vapor pressure, so that characteristic gases in the ambient air can be detected. Gas analysis is simpler compared to analysis of fluids because the characterizing constituents in the complex but uncharacteristic liquid matrix are difficult to detect and because a specimen preparation is often additionally required following the taking of a specimen, given analysis of liquids.

Fundamentally, every individual type of gas, or the constituents and composition thereof, can be measured by utilizing specific gas sensors. Many specific gas sensors are necessary in order to recognize a complex aroma that is composed of many constituents or analytes in this way. In addition to the complicated technical realization of the sensors, a number of sensors are needed, these then in turn being utilized in toto only for characterizing a few scents. Moreover, it has generally not yet been exactly scientifically documented how many and which chemical substances yield a complex aroma. Nonetheless, such an approach makes sense where the odor is caused by one or a few chemical substances recognized for this odor such as, for example, given a diabetic coma where acetone and ketone compounds are released.

Dependent on the application, concentrating the analyte can be necessary given an analyte content which is too low. This is achieved by an adsorption tube through which the specimen is conducted across an adsorbent. The analytes are thereby captured therein. By means of a following thermal desorption, the substances are released in a smaller volume, as the result of which the concentration is increased. The sensitivity of the overall system can be improved in this way.

In an embodiment of the method, the characteristic volatile constituents are supplied to a number of sensors which are analyte-non-specific, that have different sensor behavior compared to one another, and measured signals of the sensors generated by the characteristic volatile constituents are supplied to a computer for typing and clustering. An arrangement of analyte-non-specific sensors with a corresponding evaluation unit is also referred to as a electronic nose. When a number of such sensors are utilized, typically 8 through 32, each exhibiting different sensor behavior compared to one another, one analyte can produced different measured values or sensor responses, so that a fingerprint, so to speak, of the respective analyte is obtained dependent on the odor. Ideally, the sensors cover a broad spectrum of chemical properties of the gas analytes such as, for example, the molecule size, the redox behavior, etc., so that no redundant information is measured by different sensors. An exact fingerprint of the odor, however, cannot be expected. On the contrary, the aim is to construct a pool or a data bank of fingerprints, with a clustering being undertaken as to the data bank contents, for example using mathematical methods. A measured gas mixture thus is allocated to a cluster or an odor type. The sensors can be made more specific given an odor having a more specifically identified analyte composition. In this respect, the two concepts of gas analysis with the assistance of gas sensors then approach one another.

In another embodiment the characteristic volatile constituents are supplied to at least one metal oxide sensor. The sensor principle employs semiconducting metal oxides whose electrical resistance is dependent on the analyte composition. The measuring effect is based on the modification of the charge transfer with molecules in the gas phase, so that characteristic changes in the conductivity with respect to an analyte can be identified. There are numerous versions of these sensors, also as specific gas sensors.

Metal oxide sensor elements, however, cannot be employed for recognizing all possible bio-molecules, particularly large molecules. Such sensor elements must be heated to a high temperature; moreover, they modify the bio-molecule during the measuring process. A catalyst can alleviate this situation, the catalyst splitting the bio-molecules and thus enabling an investigation of the characteristic fragments. The high energy consumption of these sensors is likewise significant.

In another embodiment, the characteristic volatile constituents are supplied to at least one conductivity sensor. This type of sensor uses conductive or non-conductive polymers, and operates similarly to a metal oxide sensor. By employing different polymer materials, synthetic modification of functional groups as well as by adding different additives, a great number of sensitive versions can be produced. Fundamentally, polymer gas sensors exhibit good stability with respect to environmental influences, particularly in view of temperature. By contrast to the metal oxide sensors, they also do not react actively with the analyte (oxidation), so that no energy supply is necessary in the receptor layer. By contrast to metal oxide sensors, the sensor response in this sensor type is dependent on the atmospheric humidity because they react less sensitively to non-polar molecules.

In another embodiment, the characteristic volatile constituents are supplied to at least one quartz micro-balance sensor. Quartz micro-balance sensors (QMB sensors) are essentially composed of a piezo-electric quartz crystal. The frequency variation of the oscillating crystal, which, among other things, is modified due to masses of the analyte agglomerating on the surface, is employed as the measured property. The mass modification due to agglomeration of the analyte molecules is thereby identified. The typical operating frequency range lies between 1 MHZ and 30 MHZ. This sensor principle has practically no temperature dependency.

In a further embodiment, the characteristic volatile constituents are supplied to at least one surface acoustic wave sensor. Surface acoustic wave sensors (SAW sensors) employ the propagation of acoustic waves as a selective (variable) property for an analyte. Appropriate coatings make the sensor element sensitive to different analytes, respectively. It is usually the phase shift of an acoustic wave moving over the element that is analyzed, this being reflected by a reflector. The typical oscillator frequency lies at 430 MHZ or at 1 GHz. Particular attention must be paid to the signal stability. Temperature fluctuations have a great influence; these can be reduced either by temperature control circuits or by an additional reference SAW component. Atmospheric humidity has a similarly great influence on the measurement of the phase shift that is produced by an absorption of water molecules by the quartz and the cooling caused as a result thereof. A passivation layer of, for example, SiNe can alleviate this situation, this, among other things, shielding the quartz and likewise being capable of being a good substrate for the application of the sensitive coating.

It is sometimes not possible to operate an apparatus for the identification of the volatile constituents directly at the place of employment, for example next to a patient. According to a further embodiment of the invention, a specimen of the liquid is taken with a specimen carrier and is supplied to a specimen container connected to the sensors.

A continuous identification of a specific liquid can ensue in a further embodiment wherein the characteristic volatile constituents are extracted directly from the life form.

An apparatus for implementing the above-described inventive method has a number of analyte-non-specific sensors, with an arrangement connecting or exposing the sensors to characteristic, volatile constituents of a liquid to be identified from a living subject, and an evaluation unit connected to the sensors for typing and clustering of measured signals output by the sensors.

DESCRIPTION OF THE DRAWINGS

FIG. 1 is a schematic illustration of a first embodiment of a method for identifying a liquid secreted by a living subject in accordance with the invention, wherein the liquid is taken as a specimen.

FIG. 2 is a schematic illustration of a second embodiment of the method for identifying a liquid secreted by a living subject in accordance with the invention wherein the volatile constituents of the liquid to be analyzed are directly obtained from the subject.

DESCRIPTION OF THE PREFERRED EMBODIMENTS

FIG. 1 shows an indirect method for identifying a liquid secreted by a life form, amniotic fluid in this case, whereby the liquid is taken by a specimen smear (vaginal secretion) with a specimen carrier 2 in the form of a cotton wand. The specimen carrier 2 with the liquid to be identified is stored in a specimen container 4 and is then examined. The specimen container has an opening 6 at which volatile constituents 8 of the liquid can emerge. The volatile constituents 8 are supplied via a specimen-taking unit 10 to a measurement chamber 12 and, if necessary, to a concentrating unit 11. The specimen-taking unit 10 has a suction nozzle 14 as well as (not shown) a pump and a dosimeter or flowmeter. The concentrating unit 11 is basically composed of a small tube in which an adsorbent is located. The molecules initially retained by the adsorbent are in turn released with a heating element (thermal desorption).

A number of sensors 16, typically 8 through 32 sensors, are arranged in the measuring chamber 12. The sensors 16 have different sensor behavior, meaning that one analyte generates different sensor responses or measured signals at the individual sensors 16. The sensors 16 can be metal oxide sensors and/or conductivity sensors. For improving the quality of the conclusion about the liquid to be identified and given difficult boundary conditions, further sensor types can be used, particularly quartz micro-balances and/or surface acoustic wave sensors.

The sensors 16 are connected to a processing unit 18 that edits the sensor responses and the editorial signals are then forwarded to a computer 20 as measured values. The computer 20 contains a pool or a data bank of fingerprints of the odor to be identified, the odor of amniotic fluid in this case, and also contains fingerprints of negative specimens, for example, a secretion free of amniotic fluid in this case. A clustering is undertaken in the computer 20 using this pool or data bank, for example using mathematical methods. To that end, features are extracted from the registered measured values in a first step by multi-variant data analysis, these features being then combined in a second step, taking a known clinical diagnosis according to their affiliation to groups (clusters) into consideration. Multi-variant techniques such as, for example, principal compound analysis (PCA) are suitable for use in the second step.

For the identification itself, the sensor responses of the volatile constituents 8 of the liquid to be identified are allocated to a cluster or an odor type, using basically the same methods as in compiling the data pool. In conformity with the allocation, a conclusion is made as to whether amniotic fluid is contained in the vaginal secretion or not.

Given an adequate sensitivity of the sensors 16 to the volatile bio-molecules characterizing amniotic fluid, the volatile constituents can be measured directly at the patient without taking a prior specimen, even given dilution to the ambient air of the room. To that end, as shown in FIG. 2, the specimen-taking unit 10 is placed in direct communication with the patient.

The specimen-taking unit 10 with the sensors 16, including the processing circuit 18 and the evaluation computer 20, are obtainable in generic form from the Nennartz Company in Tübingen, Germany, under the designation MOSES II.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for identifying a liquid secreted by a living subject, comprising the steps of obtaining characteristic volatile constituents of a liquid to be identified from a living female subject, and identifying whether said liquid is amniotic fluid by said characteristic volatile constituents to detect at least one of a premature amnion rupture and an intrauterine infection.

2. A method as claimed in claim 1 wherein the step of identifying whether said liquid is amniotic fluid comprises supplying said characteristic volatile constituents to a plurality of analysand-non-specific sensors respectively exhibiting different sensor behavior relative to each other, obtaining respective measured signals from said plurality of sensors dependent on said characteristic volatile constituents, supplying said measured signals to a computer, and, in said computer, typing and clustering said measured signals to identify whether said liquid is amniotic fluid.

3. A method as claimed in claim 2 wherein the step of supplying said characteristic volatile constituents to a plurality of analyte-non-specific sensors includes supplying said characteristic volatile constituents to at least one metal oxide sensor.

4. A method as claimed in claim 3 wherein the step of supplying said characteristic volatile constituents to a plurality of analyte-non-specific sensors includes supplying said characteristic volatile constituents to at least one conductivity sensor.

5. A method as claimed in claim 4 wherein the step of supplying said characteristic volatile constituents to a plurality of analyte-non-specific sensors includes supplying said characteristic volatile constituents to at least one quartz micro-balance sensor.

6. A method as claimed in claim 5 wherein the step of supplying said characteristic volatile constituents to a plurality of analyte-non-specific sensors includes supplying said characteristic volatile constituents to at least one surface acoustic wave sensor.

7. A method as claimed in claim 2 wherein the step of supplying said characteristic volatile constituents to a plurality of analyte-non-specific sensors includes supplying said characteristic volatile constituents to at least one conductivity sensor.

8. A method as claimed in claim 2 wherein the step of supplying said characteristic volatile constituents to a plurality of analyte-non-specific sensors includes supplying said characteristic volatile constituents to at least one quartz micro-balance sensor.

9. A method as claimed in claim 2 wherein the step of supplying said characteristic volatile constituents to a plurality of analyte-non-specific sensors includes supplying said characteristic volatile constituents to at least one surface acoustic wave sensor.

10. A method as claimed in claim 1 wherein the step of obtaining said characteristic volatile constituents comprises taking a specimen of said liquid with a specimen carrier, and placing said liquid in said specimen carrier at a location for interacting with said plurality of sensors.

11. A method as claimed in claim 1 wherein the step of obtaining said characteristic volatile constituents comprises extracting said characteristic volatile constituents directly from a living subject.

* * * * *